United States Patent
Samah et al.

(10) Patent No.: US 7,718,552 B2
(45) Date of Patent: May 18, 2010

(54) NANOSTRUCTURED TITANIA

(75) Inventors: Zuruzi Abu Samah, Santa Barbara, CA (US); Noel C. MacDonald, Santa Barbara, CA (US); Marcus Ward, Goleta, CA (US); Martin Moskovits, Santa Barbara, CA (US); Andrei Kolmakov, Buellton, CA (US); Cyrus R. Safinya, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 606 days.

(21) Appl. No.: 11/397,165

(22) Filed: Apr. 4, 2006

(65) Prior Publication Data
US 2010/0086734 A1    Apr. 8, 2010

Related U.S. Application Data

(60) Provisional application No. 60/667,667, filed on Apr. 4, 2005.

(51) Int. Cl.
  *H01L 21/469* (2006.01)
(52) U.S. Cl. ............... 438/785; 257/763; 257/770; 257/E21.168; 257/E21.592; 257/E23.017; 438/656; 438/685; 977/781; 977/784; 977/811; 977/888; 977/890
(58) Field of Classification Search .......... 257/763, 257/764, 770, E21.168, E21.592, E23.017; 438/785, 656, 685; 977/781, 784, 811, 888, 977/890, 932
See application file for complete search history.

(56) References Cited

U.S. PATENT DOCUMENTS

| | | | | |
|---|---|---|---|---|
| 4,228,128 A * | 10/1980 | Esper et al. | .................... | 422/98 |
| 6,475,867 B1 * | 11/2002 | Hui et al. | ..................... | 438/299 |
| 6,946,597 B2 * | 9/2005 | Sager et al. | ................. | 136/263 |
| 7,208,327 B2 * | 4/2007 | Gstrein et al. | .................. | 438/10 |
| 2005/0098205 A1 * | 5/2005 | Roscheisen et al. | ......... | 136/263 |
| 2005/0224360 A1 * | 10/2005 | Varghese et al. | ............ | 205/171 |

OTHER PUBLICATIONS

Zuruzi et al., Integrating Biomaterials into Microsystems: Formation and Characterization of Nanostructured Titania, Mat. Res. Soc. Symp. Proc. vol. 820, O9.4.1-O9.4.6.*
Zuruzi et al., Facile Fabrication and Integration of Patterned Nanostructured TiO2 for Microsystems Applications, Adv. Funct. Mater. 2005, 15, No. 3, 396-402.*
Gouma et al., Fabrication of Free-Standing Titania-Based Gas Sensors by the Oxidation of Metallic Titanium Foils, J. Am. Ceram. Soc., 83 [4], 1007-1009.*

(Continued)

*Primary Examiner*—Anh Phung
*Assistant Examiner*—Michael Lulis
(74) *Attorney, Agent, or Firm*—Gates & Cooper LLP

(57) ABSTRACT

A method and device of nanostructured titania that is crack free. A method in accordance with the present invention comprises depositing a Ti film on a surface, depositing a masking layer on the Ti film, etching said masking layer to expose a limited region of the Ti film, the limited region being of an area less than a threshold area, oxidizing the exposed limited region of the Th.ucsbi film, and annealing the exposed limited region of the Ti film.

20 Claims, 12 Drawing Sheets

OTHER PUBLICATIONS

Zuruzi et al., Low-cost integrated sensors utilizing patterned nanostructured titania arrays fabricated using a simple process. Abstract of oral presentation at the Fall Meeting of the Materials Research Society, Boston, Nov. 29-Dec. 3, 2004.*

Ruiz et al., Surface activation by Pt-nanoclusters on titania for gas sensing applications, Mat. Sci. Eng. C 19 (2002), 105-109.*

DeRosa et al., "Formation of Nanostructured Titania: Effect of Thickness on Oxidation Kinetics of Titanium Thin Films in Aqueous Hydrogen Peroxide," Advanced Engineering Materials, 2006, 8, No. 1-2, pp. 77-80.

Zuruzi et al., "Highly Sensitive Gas Sensor Based on Integrated Titania Nanosponge Arrays," Applied Physics Letters 88, 102904, 2006, pp. 1-3.

Zuruzi et al., "Nanostructured TiO2 Thin Films as Porous Cellular Interfaces," Institute of Physics Publishing, Nanotechnology 17, 2006, pp. 531-555.

Zuruzi et al., "Fabrication and Characterization of Patterned Micrometre Scale Interpenetrating Au-TiO2 Network Nanocomposites," Institute of Physics Publishing, Nanotechnology 16, 2005, pp. 1029-1034.

* cited by examiner

FIG. 4(a)    FIG. 4(b)
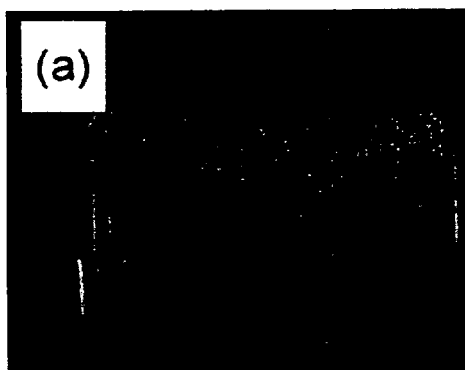
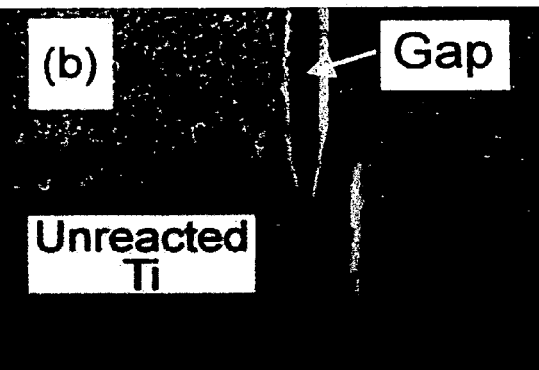
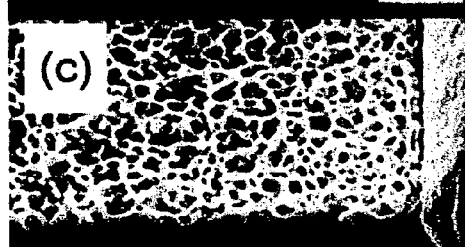
FIG. 4(c)    FIG. 4(d)

FIG. 11(a)
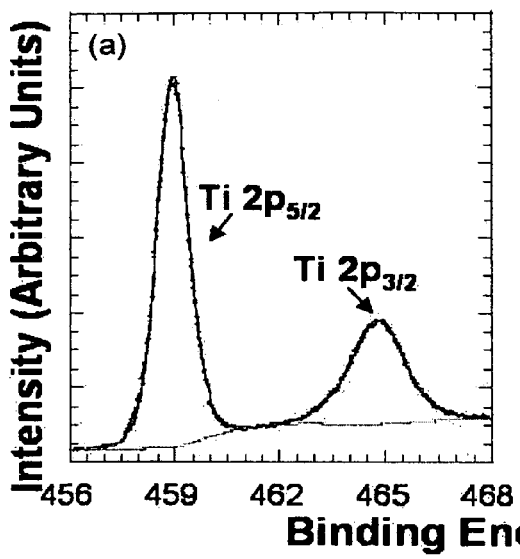
FIG. 11(b)
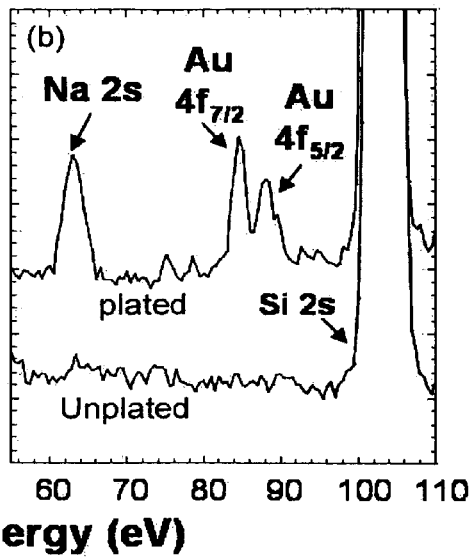
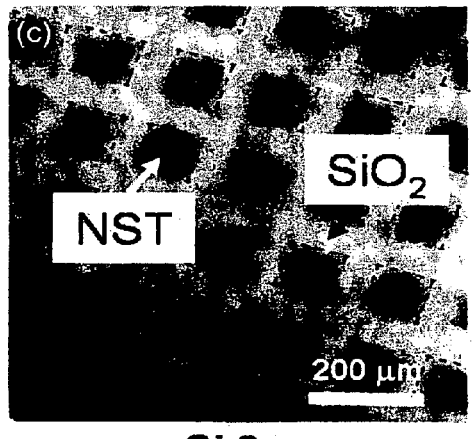
Si 2p
FIG. 11(c)
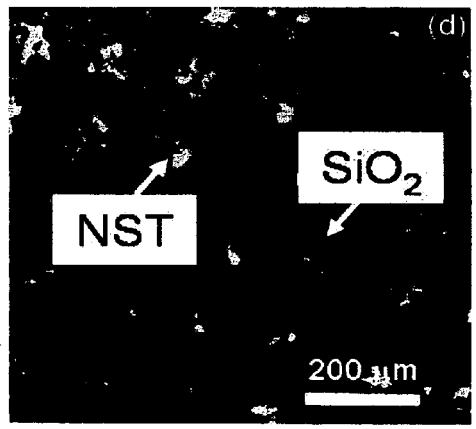
Au 4f
FIG. 11(d)

NANOSTRUCTURED TITANIA

CROSS-REFERENCE TO RELATED APPLICATIONS

This application claims the benefit under 35 U.S.C. Section 119(e) of co-pending and commonly-assigned U.S. provisional patent application Ser. No. 60/667,667, filed Apr. 4, 2005, entitled "NANOSTRUCTURED TITANIA," by Zuruzi A. Samah et al., which application is incorporated by reference herein.

BACKGROUND OF THE INVENTION

1. Field of the Invention

The present invention relates generally to a method of forming patterned nanostructured titania (NST) features, and in particular for forming NST features for various electronic applications such as chemical sensing, wear-resistant electrical contacts and photovoltaics.

2. Description of the Related Art

Patterned nanoporous titania (NST) thin films are well known in many prior reports. For instance, NST has been used in chemical detection systems, catalysis and solar energy conversion. In one widely used conventional method (called the sol-gel method), patterned features of $TiO_2$ are made by the hydrolysis and condensation of metal alkoxide precursors. The metal alkoxide precursors, in liquid form, are deposited on a substrate and subsequently decomposed to form a titania gel film. Various techniques have been used to pattern the $TiO_2$ film such as reactive ion etching, embossing and laser trimming. It is noted that except reactive ion etching, other techniques used with this method are not compatible with high-volume semiconductor manufacturing processes. Patterning of the $TiO_2$ film is done either before or after an annealing step in which the film is heated at elevated temperature to convert the amorphous titania gel into crystalline $TiO_2$. In addition, special precautions are usually required to ensure crack formation does not occur and carbon, from the organic precursors, is not incorporated in or on the nanostructured titania features.

In another known method, paste containing titanium dioxide powders is screen printed at desired locations on components using hard mask; example metal mask. The use of hard mask means that accurate alignment techniques are needed to deposit the paste at desired locations on the substrate. Also the probability of adjacent paste developing bridges increases as the pitch decreases, thus lowering process yield.

In yet another known method, self-assembled monolayers (SAMs) are selectively deposited at locations on which $TiO_2$ pads are desired. Selective deposition of $TiO_2$ films occurs by interactions of functional group of the self-assembled monolayers with Ti-containing precursors. Because surface coverage of SAM is, in most cases, not high, this method results in poor yield especially when large-area substrates are used. In addition, relatively long time—up to a few hours—is required for deposition of $TiO_2$ using this method. In addition, edge acuity, or the ratio of standard deviation to the mean of a sample of pattern widths, of titania features formed using this technique is relatively poor, namely, about 2.1% in the state of the art. This latter problem makes it extremely difficult to use this method to form submicrometer features with very small separation.

With the persistent effort to trim cost and the ever-pervading trend of miniaturizing electronic components, the electronics industry is constantly moving towards using larger diameter wafers to increase yield and hence drive cost down, and making features on integrated circuits smaller and closer to each other. It is, therefore, becoming increasingly difficult to form miniaturized features of porous $TiO_2$ in integrated circuitry.

Formation of porous titania by reacting aqueous hydrogen peroxide (aq. $H_2O_2$) solution with thick Ti sheets, Ti powder and unpatterned Ti films is already known in prior art scientific literature. Similarly, formation of a porous titania layer by reacting Ti with aqueous NaOH solutions had been reported. However, in all these cases, titania layers formed by reacting aqueous hydrogen peroxide have high crack density and delaminated extensively from the underlying substrate making them unsuitable for applications in integrated microelectronic circuits.

It can be seen, then, that there is a need in the art for titania layers in microelectronic applications. It can also be seen that there is a need in the art for titania layers that are easily produced that do not have high crack densities and do not delaminate from the underlying substrate.

SUMMARY OF THE INVENTION

To minimize the limitations in the prior art, and to minimize other limitations that will become apparent upon reading and understanding the present specification, the present invention describes a method and device of nanostructured titania that is crack free.

A method in accordance with the present invention comprises depositing a Ti film on a surface, depositing a masking layer on the Ti film, etching said masking layer to expose a limited region of the Ti film, the limited region being of an area less than a threshold area, oxidizing the exposed limited region of the Ti film, and annealing the exposed limited region of the Ti film.

Such a method further optionally includes oxidizing the exposed limited region of the Ti film includes aging the exposed limited region of the Ti film using an aqueous hydrogen peroxide solution, the threshold area has a dimension of about 20 µm, adding dopants to the Ti film, adding dopants includes soaking the exposed limited region of the Ti film in a dopant-containing solution after aging, adding dopants includes coating the exposed limited region of the Ti film with dopant species after annealing, depositing and patterning a metal electrode on the exposed limited region of the Ti film after annealing, infiltrating the exposed limited region of the Ti film with an electrically conductive metal to form an interpenetrating network nanocomposite, etching the masking layer exposes a plurality of limited regions of the Ti film to form an array of pads, selectively metallizing the array of pads to interconnect the pads, infiltrating a metal into pores in the exposed limited region of the Ti film, depositing the Ti film on a surface comprises depositing the Ti film on a flexible substrate, and etching the masking layer exposes a plurality of limited regions of the Ti film to form an array of pads, the method further including metallizing the array to interconnect the pads.

A patterned, crack-free nanostructural titania (NST) element in accordance with the present invention comprises a substrate, a Ti film deposited on the substrate, and a masking layer having at least one aperture exposing a region of the Ti film, the region having a dimension of about 20 µm; wherein the exposed region of the Ti film is oxidized to create at least one porous $TiO_2$ region.

Such a device further optionally includes an electrical contact on the porous $TiO_2$ region, the substrate being flexible, an electrically conducting metal infiltrated in the porous $TiO_2$ region, the exposed region of the Ti film being oxidized to create a plurality of porous $TiO_2$ for forming an array of pads, the porous $TiO_2$ region further comprises pores ranging in diameter from about 15 nm to about 150 nm, and adding dopants to the Ti film.

The issues of crack formation in $TiO_2$ and delamination of $TiO_2$ features from the underlying substrate can, however, be eliminated by oxidizing exposed surfaces of Ti thin films that have been masked to below a threshold area.

For example by reacting patterned Ti films of 20 µm squares with hydrogen peroxide, cracks can be eliminated in $TiO_2$ features formed. In addition, $TiO_2$ features thus formed have better edge acuity than those formed using the SAMs technique. Furthermore, the issue of carbon incorporation does not arise since high purity Ti film is used instead of organic precursors. In addition, the technique disclosed uses process tools and material sets that are already in use in the semiconductor industry. Hence the technique is compatible with current manufacturing processes.

It is the object of the invention described in this disclosure to provide a method of forming, on an electronic component, patterned NST elements that are crack free, have high edge acuity and with sizes from about 300 micrometers or less. In another aspect, this disclosure provides a method of constructing a chemical sensing element, comprising providing patterned NST features, fabricated using the aforementioned process, on an electronic circuit and depositing electrodes on the NST features. In a further aspect, this disclosure provides a method of constructing patterned nanocomposites comprised of metal and NST features fabricated using the aforementioned process, suitable for use as wear resistant electrical contacts on electronic components. In still another aspect of the invention, the NST elements fabricated in accordance with the foregoing process are porous and have pores of various selectable diameters. The elements of the invention can be incorporated in microcircuits and are biocompatible.

BRIEF DESCRIPTION OF THE DRAWINGS

Referring now to the drawings in which like reference numbers represent corresponding parts throughout:

FIGS. 4(a)-4(d) are cross-sectional micrographs obtained after milling ns-titania layers and membranes;

FIGS. 11(a) through 11(d) illustrate selective XPS scans of NST elements; and

DETAILED DESCRIPTION OF THE PREFERRED EMBODIMENTS

In the following description, reference is made to the accompanying drawings which form a part hereof, and which is shown, by way of illustration, several embodiments of the present invention. It is understood that other embodiments may be utilized and structural changes may be made without departing from the scope of the present invention.

Overview and Related Publications Incorporated by Reference

The present invention relates to formation of nanostructured titania (NST) from patterned Ti films. To prove the effectiveness of patterning to reduce and eliminate crack formation, NST was also formed on blanket (unpatterned) Ti films.

Additional description of the process for fabricating crack fee nanostructured titania (NST, or ns-titania) is found in Appendices A-H of provisional patent application Ser. No. 60/667,667, the disclosure and appendices of which are an integral part of this application and which are also hereby incorporated herein by reference.

Experimental Setup

Figure 1:
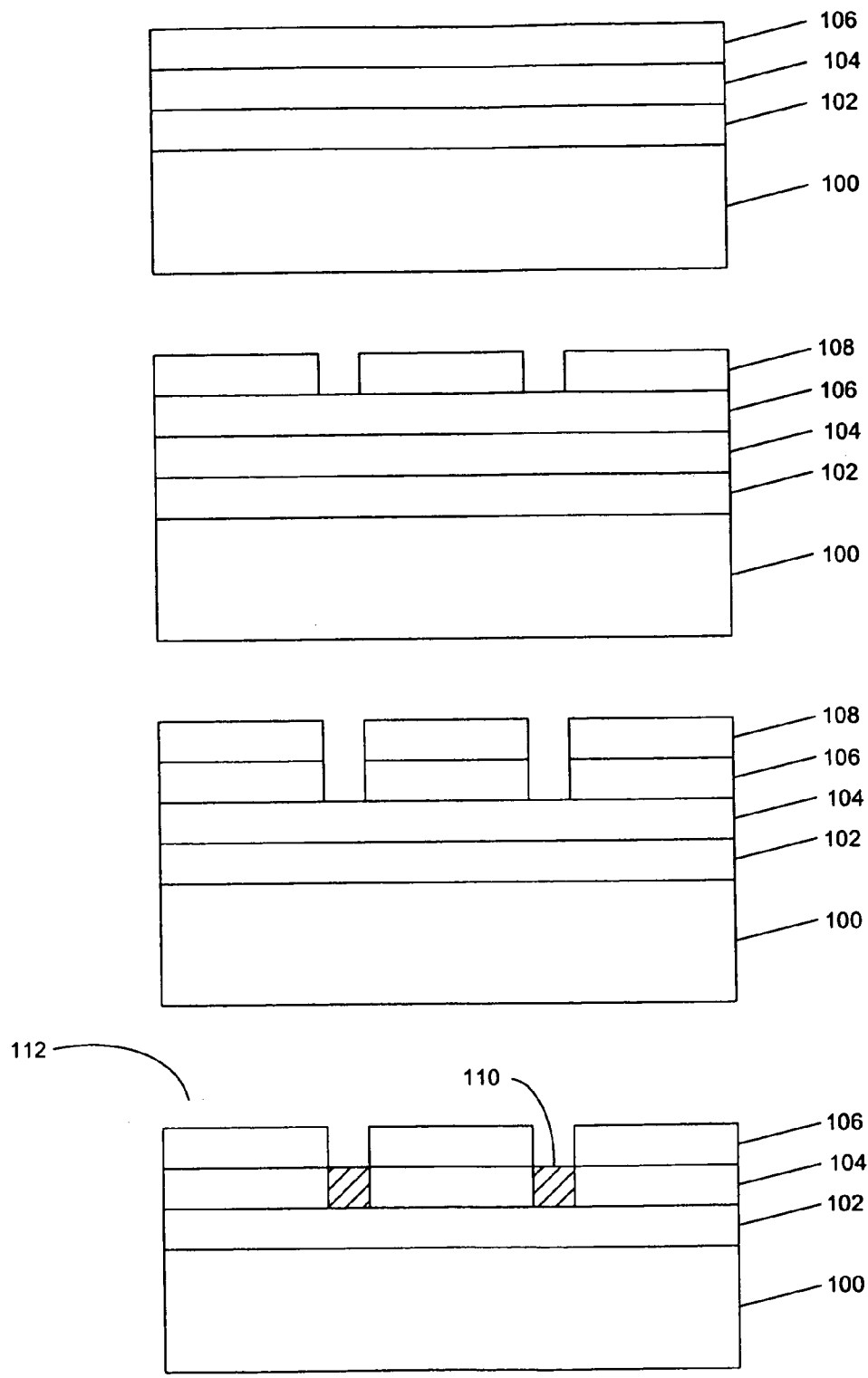
FIG. 1 is a schematic illustration of the process of the invention.

A schematic flow diagram for formation of NST on patterned Ti pad arrays is shown in FIG. 1.

Initially, substrate 100, which is typically a 2.5 cm square piece of either N-type Silicon <100> or glass, but can be other substrates, such as compound semiconductors, e.g., GaAs, InP, etc., and can also be flexible substrates, e.g., polymers such as Kapton™, without departing from the scope of the present invention. Substrate 100 has a layer 102 of silicon dioxide ($SiO_2$) grown on top of substrate 100.

For glass substrates 100, a 1 µm thick $SiO_2$ layer was deposited by Plasma Enhanced Chemical Vapor Deposition (PECVD), although other growth methods can be used without departing from the scope of the present invention. The $SiO_2$ layer 102 was cleaned with ultrasonic agitation for 5 min each, sequentially, in acetone, 2-propanol and de-ionized (DI) water, and blown dry with nitrogen prior to deposition of Ti film 104.

A Ti film 104 is then deposited using electron beam evaporation onto the layer 102. Although evaporation was used, other methods of depositing Ti, such as sputtering, can be used without departing from the scope of the present invention.

For depositing blanket Ti films 104, Silicon substrate 100 pieces were used as cleaned. Process pressure during evaporation of Ti films was ~$5.0 \times 10^{-7}$ Torr. All Ti sources used were of 99.995% purity or better and cleaned by pre-evaporation to remove native oxide layer on surface.

Another layer 106 of silicon dioxide was then deposited using PECVD, using silane ($SiH_4$) and nitrous oxide ($N_2O$) precursors at 250° C. This layer 106 is a mask layer, and can be made from other materials without departing from the scope of the present invention.

A layer 108 of photoresist (PR) was deposited on the silicon dioxide layer and patterned using photolithographic techniques. The pattern on the PR layer 108 is then transferred to the silicon dioxide layer 106 by etching, typically through the use of $CHF_3$ gas. After patterning, the PR layer 108 is removed, typically by soaking in acetone.

Areas 110 of NST were formed by aging the samples 112 in an aqueous $H_2O_2$ solution. Prior to aging, Ti film 104 was acid pickled in dilute hydrochloric acid for about 2 min to remove any native oxide layer, rinsed in DI water and then blown dry with nitrogen. Aging was done in an oven at 80±2°

C. in ambient air. Samples were stored in a vacuum box prior to analysis. Crystal structure was analyzed by X-ray diffraction in Bragg-Brentano configuration using CuK$_\alpha$ radiation (1.5406).

Structural characterization of sample 112 was done using an FEI dual beam focus ion beam system equipped with Ga ion and electron columns for high resolution machining and imaging operations, respectively. Surface chemical species was determined using a Kratos Axis Ultra X-ray Photoelectron Spectroscopy (XPS) system. High resolution XPS scans were obtained with monochromated Al K$_\alpha$ source (1486.6 eV) and 20 eV pass energy with steps of 0.05 eV at a base pressure of $7.5 \times 10^{-9}$ Torr. Transmission electron microscopy (TEM) was carried out using an FEI Sphera T20 machine operating at 200 kV.

SEM Micrographs

Figures 2A, 2B:
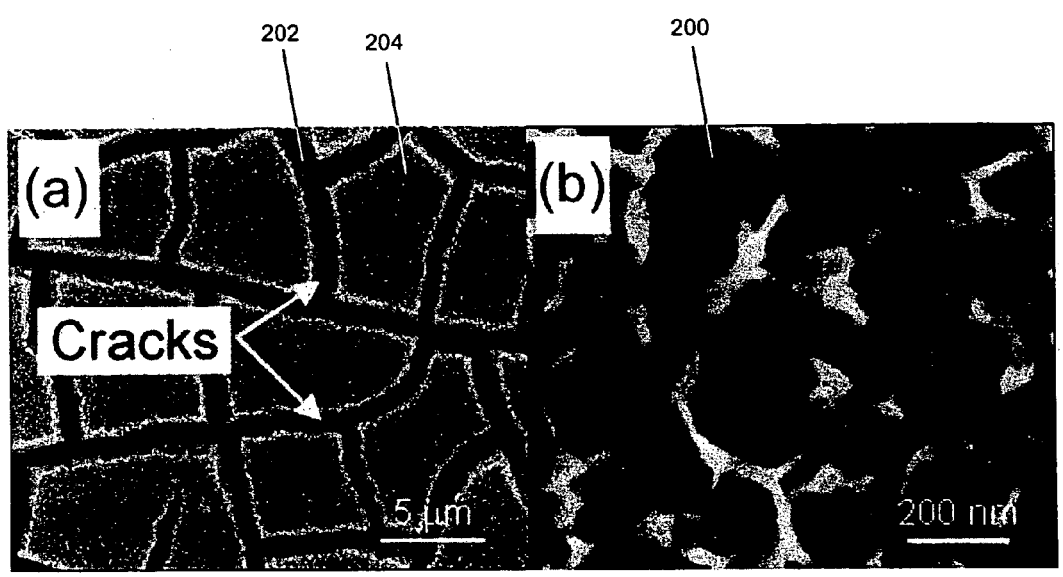
FIGS. 2(a)-2(b) are SEM micrographs of unpatterned Ti thin films showing high crack density in ns titania formed on unpatterned Ti surfaces.

FIGS. 2(a) and 2(b) illustrate morphology and crack formation in ns-titania layers formed on unpatterned Ti surfaces.

SEM micrographs of unpatterned Ti films after aging in aq. $H_2O_2$ revealed formation of NST layers 110 with high crack density, as shown in FIGS. 2(a) and 2(b). High resolution SEM micrographs shows that NST layers 110 formed consist of walls of pores 200 having thicknesses ranging from 25-50 nm and pore 200 diameters ranging from 50-200 nm (seen in FIG. 2(b)).

The high crack 202 density results in the formation of "grains" 204 of about 5-7.5 μm average diameter as shown in FIG. 2(a). Cracks 202 on NST layers 110 formed on thin films 104 extend from the surface to the thermally grown $SiO_2$ layer 102 and resulted in complete delamination of NST layers 110 especially after prolonged oxidation times.

FIGS. 3(a)-(f) illustrate SEM micrographs of NST layers 110 formed from patterned Ti square pads of various dimensions in accordance with the present invention.

By using Ti films 104 that have been patterned below a threshold dimension, crack formation on NST layers 110 was eliminated. As seen in FIGS. 3(a)-(f), where the thickness of the Ti layer 104 is 2.0 μm, cracking is most extensive on 100 μm pads 300 of Ti layer 104 (shown in FIG. 3(a)), and resulted in the NST 110/unreacted Ti bilayer 104 peeling off from the Si substrate 100 shown in the inset of FIG. 3(a).

Cracking is significantly reduced for 70 μm pads 302 and for arrays of 20 and 5 μm pads 304 and 306, respectively, crack formation is eliminated. Also NST arrays of 20 and 5 μm pads have excellent adhesion to the underlying $SiO_2$ layer. It is noted that cracks were not formed on 20 μm and 5 μm pads 304 and 306 even after annealing at 300° C. for 8 hr when the pads shrunk.

Figures 3A, 3B, 3C, 3D, 3E, 3F:
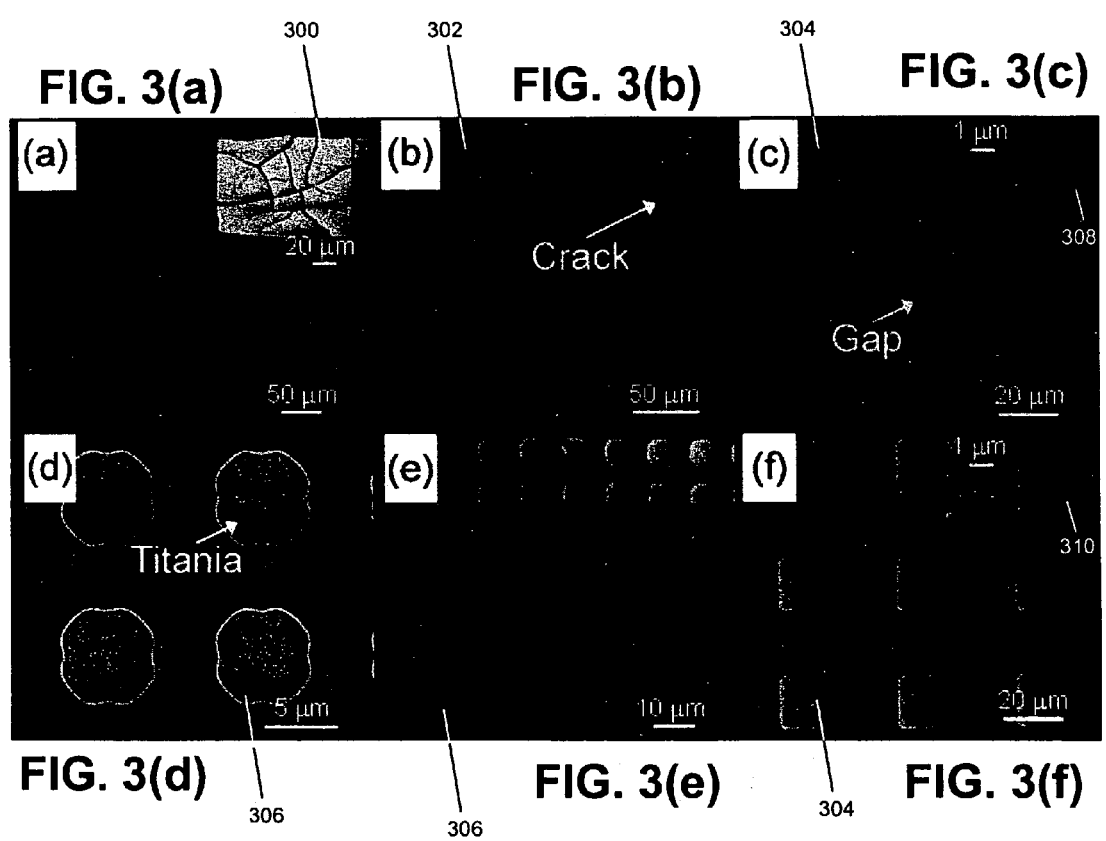
FIGS. 3(a)-3(f) are SEM micrographs of ns-titania layers.

For 20 μm pads, the gap width 308 is about 0.7 μm after drying in air but increased to a gap width 310 of about 1.2 μm after annealing at 300° C. for 8 hr, as shown in the insets of FIGS. 3(c) and 3(f) respectively. For arrays of 5 μm pads 306, width of gap before and after annealing is estimated to be about 50 nm and 90 nm, respectively.

The effectiveness of the method in eliminating cracks 202 is evident in FIG. 3(e), in which all the 5 μm NST pads 306 remain crack free. Also the edge acuity of pads 304. 306 fabricated using the disclosed process is 0.44%; much lower than those fabricated using SAMS yields patterns with 2.1% edge acuity.

Oxidation of Titanium

FIGS. 4(a)-4(d) are cross-sectional micrographs obtained after milling ns-titania layers and membranes showing the oxidation of the titanium layer.

By controlling the aging time in aq. $H_2O_2$ solution, complete or partial oxidation of Ti films is achieved. FIGS. 4(a) and 4(b) are cross-sectional SEM micrographs obtained after focus ion beam milling of an NST layer grown on 2.0 μm thick evaporated Ti pads 304 after aging in 10% aq. $H_2O_2$ for 2.5 hrs at 80° C., which show partial oxidation of the Ti pads 304. The NST/unreacted Ti interface is robust with no delamination.

FIGS. 4(c) and 4(d) are cross-sectional SEM micrographs of supported $TiO_2$ membranes formed by fully oxidizing 0.35 μm thick evaporated Ti films by aging in 10% aq. $H_2O_2$ for 3.5 hrs at 80° C. Although lengthy oxidation times, on the order of a few hours, are reported herein, in-situ kinetics studies show that the oxidation reaction is completed, that is the Ti is consumed, after just a few minutes; for example, 500 nm Ti films 104 will be completely oxidized in less than 45 minutes. Although the Ti films were completely oxidized no crack was observed at the NST/T-$SiO_2$ interface, which indicates excellent adhesion of the pad to the underlying T-$SiO_2$ substrate 100.

Formation of Anatase $TiO_2$

Figure 5A:
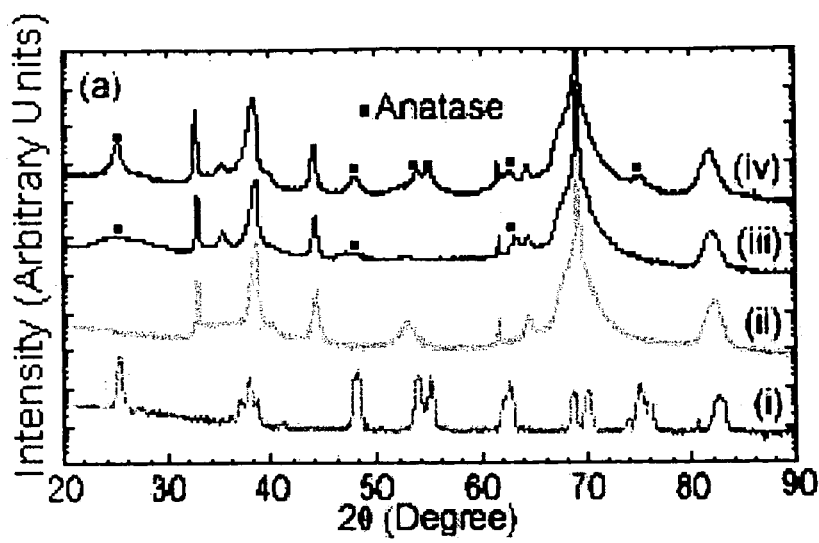
FIG. 5(a) is an XRD spectra showing the phase evolution of titania.

X-Ray Diffraction (XRD) studies show that amorphous $TiO_2$ and nano-crystals of anatase $TiO_2$ polymorph were formed after aging and the amorphous phase transforms to anatase upon annealing. FIG. 5(a) shows XRD spectra of evaporated Ti film, as-aged and annealed $TiO_2$ layer formed from evaporated blanket Ti films. Spectra of the sample aged in 10% aq. $H_2O_2$ solution for 2.5 hr at 80° C. exhibit Ti peaks, which correspond to unreacted Ti in aged films and three broad peaks at 2θ values of 25.20°, 47.97° and 62.68° which can be assigned to anatase {101}, {200} and {204} planes. The broadness and low intensity of these peaks suggest that as-formed titania layer consists of anatase nano-crystals in a largely amorphous titania matrix.

Upon annealing at 300° C. for 8 hr, these peaks sharpened significantly and increased in intensity. The peak sharpening and intensity increase upon annealing are due to transformation of the amorphous phase to anatase, which also agrees with the appearance of additional peaks at 2θ values of 53.91°, 54.95° and 75.04°. These latter peaks correspond to {105}, {211} and {215} reflections of anatase. All anatase peaks in the spectrum of annealed $TiO_2$ layer match perfectly to corresponding ones in spectrum collected from reference $TiO_2$ anatase powder (Alfa Aesar, 99.6%). No peaks from other $TiO_2$ polymorphs are observed in spectra of annealed samples. Hence, XRD data indicate that only nano-crystals of anatase $TiO_2$ and an amorphous titania phase are formed after aging. Subsequent annealing transforms the amorphous phase to anatase.

Figure 5B:
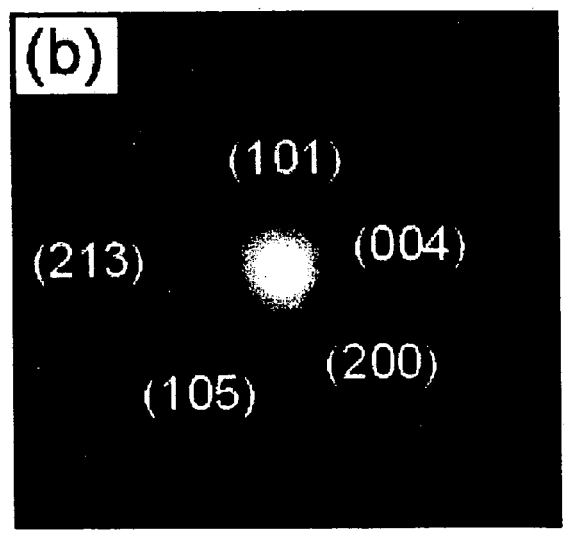
FIG. 5(b) is a selected area electron diffraction showing the formation of anatase after annealing.

The formation of anatase is confirmed by results of Selected Area Electron Diffraction, performed in a Transmission Electron Microscope (TEM), of a cross-sectioned sample; see FIG. 5(b). Electron diffraction images at selected locations of the exposed NST regions consist of sharp concentric rings assignable uniquely to polycrystalline anatase. No evidence of other phases of titania was observed.

It is noted that whilst in the above described embodiment the NST features are formed on glass and Si chips, they could of course be formed just as well on other substrates or on some other electronic component without departing from the scope of the present invention.

Dopant Impurity Introduction

In addition, although in the above-described embodiment the NST features have no impurities incorporated, dopants may be intentionally added by soaking the titania gel formed after aging in aq. $H_2O_2$ solution in a suitable solution containing the dopants. For example to incorporate Pt species, the titania gel features are soaked in platinum chloride solution and subsequently annealed. In this way the properties of the NST features may be tuned accordingly for various applications. In another embodiment, dopants may be added after the NST features have been annealed. In these cases, dopants species may be coated on the surfaces of the NST (anatase) features.

Another aspect of the disclosure provides a semiconductor device structure having an NST pad and metal electrodes formed thereon, the NST pad having been fabricated using the above disclosed process and the metal electrodes deposited by techniques such as evaporation or sputtering.

Figure 6A:
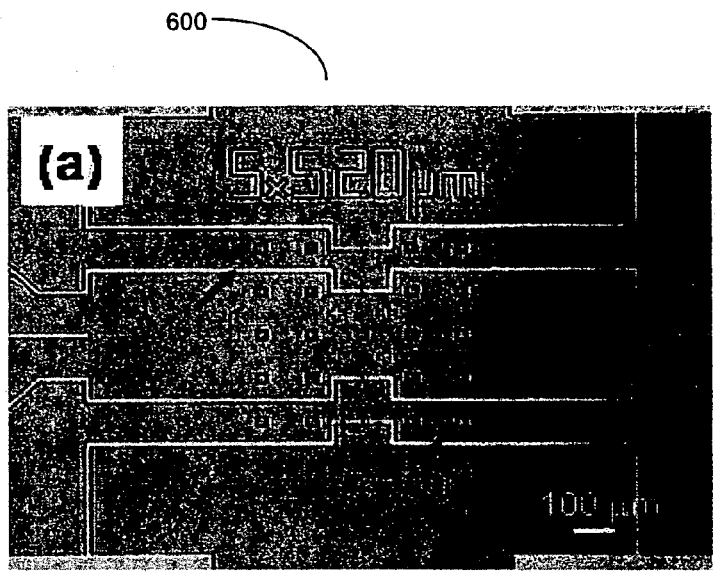
FIG. 6(a)-6(b) are an optical micrographs of titania pad arrays including integrated sensing elements.
Figure 6B:
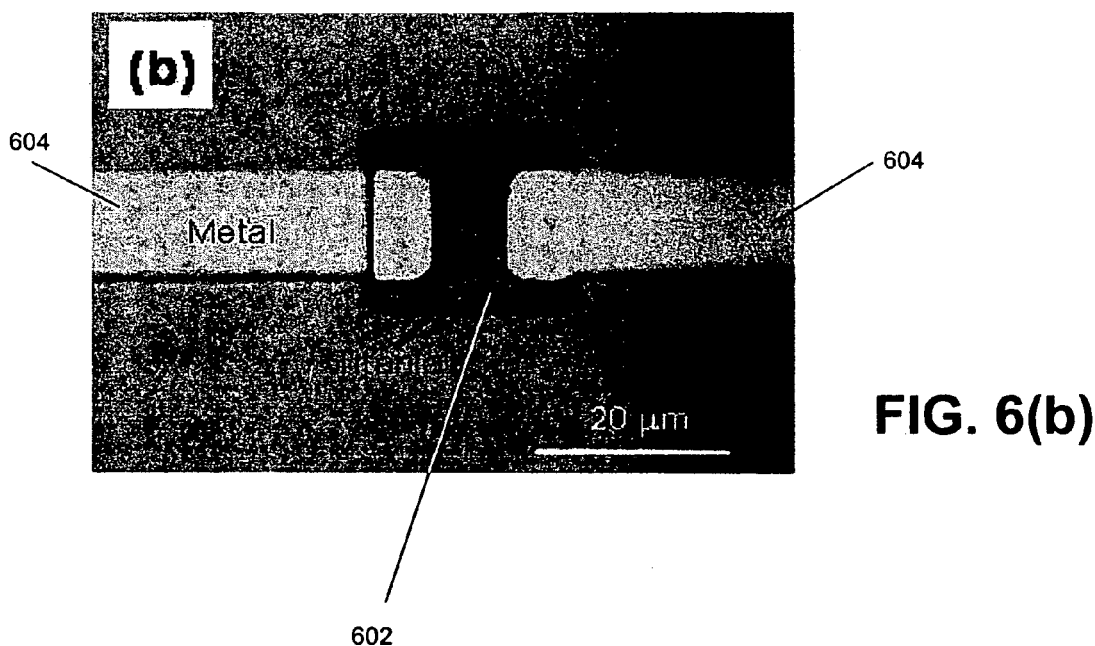

FIG. 6(a) shows the layout and structure of a prototype gas sensor 600 utilizing NST pads as sensing elements consisting of a 5 by 5 array of square NST pads, each 20 μm wide. In principle, each of the pads could be individually addressable. For simplicity we have metallized only a few, selected pads of the 5 by 5 array with 10 μm wide metal lines. Moreover, further scaling down of the device is feasible with currently available microelectronics process tools. FIG. 6b shows a high magnification image of a pad 602 that has been metallized with Ti/Pt multilayer electrodes 604.

Figure 7A:
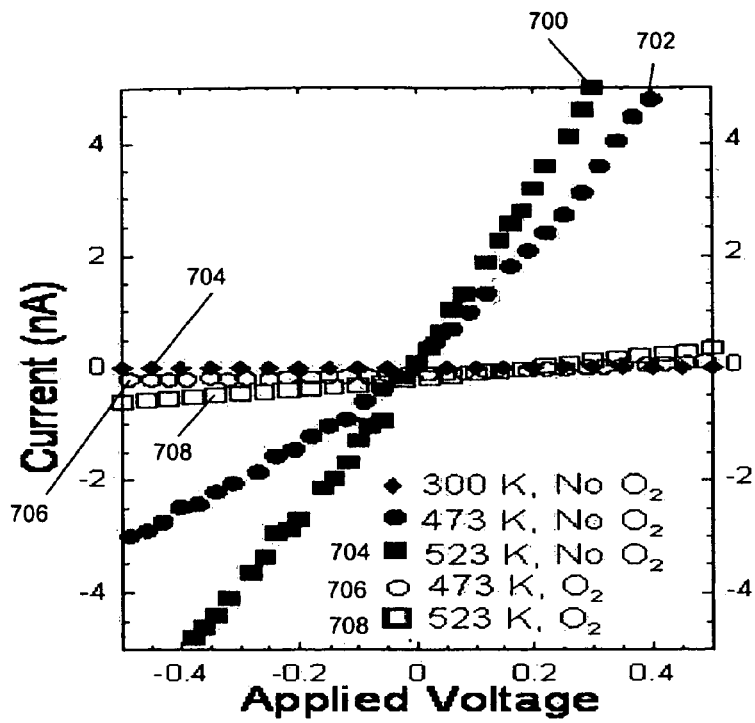
FIGS. 7(a) and 7(b) illustrate current-voltage characteristics of an NST pad.

FIGS. 7(a) and (b) illustrates the performance of the prototype sensor of FIG. 6(a) in detecting oxygen. Sensing experiments were carried out in a vacuum chamber equipped with microprobe contacts for current-voltage (I-V) measurements. The oxygen partial pressure in the test chamber was controlled by means of a pulsed needle valve and confirmed using an ion gauge. A halogen lamp heater was used to raise the sensor assembly to the desired temperature, which was measured using a K-type thermocouple.

Figure 7B:
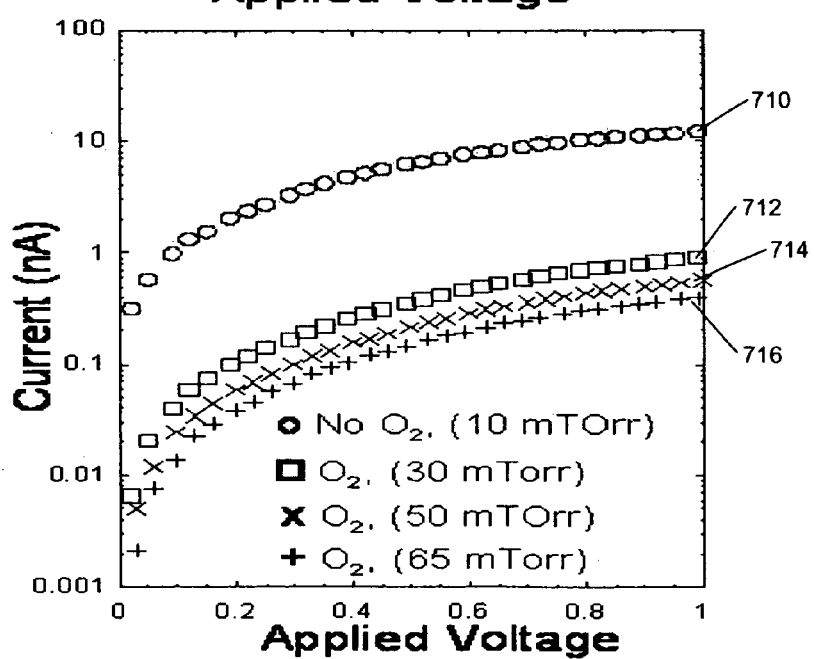

FIGS. 7(a) and 7(b) show the I-V characteristics 700-716 of an NST pad in vacuum and under oxygen exposure at various $O_2$ partial pressures ranging from 30 to 80 mTorr. The linear I-V characteristics obtained indicate that contacts between the Ti/Pt electrodes and the NST pads were Ohmic at the temperatures utilized. The conductance of the NST pads is very sensitive to the presence of oxygen and changes monotonically with oxygen partial pressure as shown by characteristics 712-716. In the presence of $O_2$, conductance of the pad is approximately an order of magnitude less than that in vacuum, as seen by the difference between characteristics 700-702 and characteristics 704-708. This high sensitivity to $O_2$ is also illustrated in FIG. 7(b) where $O_2$ pressure variations in the mTorr range were easily distinguishable. Assuming $O_2$ to be entrained in an unreactive gas such as nitrogen, these mTorr pressure variations at 523 K correspond to ppm detectivity by an NST pad. By adding dopants to the NST layer 110, significant enhancement and tuning of sensing properties may be realized.

Another aspect of the disclosure provides a structure comprising an NST 110 pad, having been fabricated using the above disclosed process, and electrically conducting metals such as Ag, Au, Ni, Pt, Pd or their alloys that are infiltrated into and fill pores of the NST pad forming interpenetrating network nanocomposites. The metals may be infiltrated into pores of the NST features using processes such as electroless deposition or other chemical means. Such composites comprising of nanostructured titania and interpenetrating metal phases may be used as wear-resistant electrical contacts in miniaturized switches. Thin films of Au and its alloy have been widely used as contact material in micro-switch devices because of their low-resistivity and oxidation resistance. However, they suffer from wear and stiction that shorten device lifetimes. In contrast, titania films formed using sol-gel have excellent wear resistance. Au—$TiO_2$ interpenetrating network nanocomposites would have functionalities of its constituents such as wear resistance of $TiO_2$ while simultaneously possessing the high electrical conductivity of Au due to the continuity of both phases.

Figure 8:
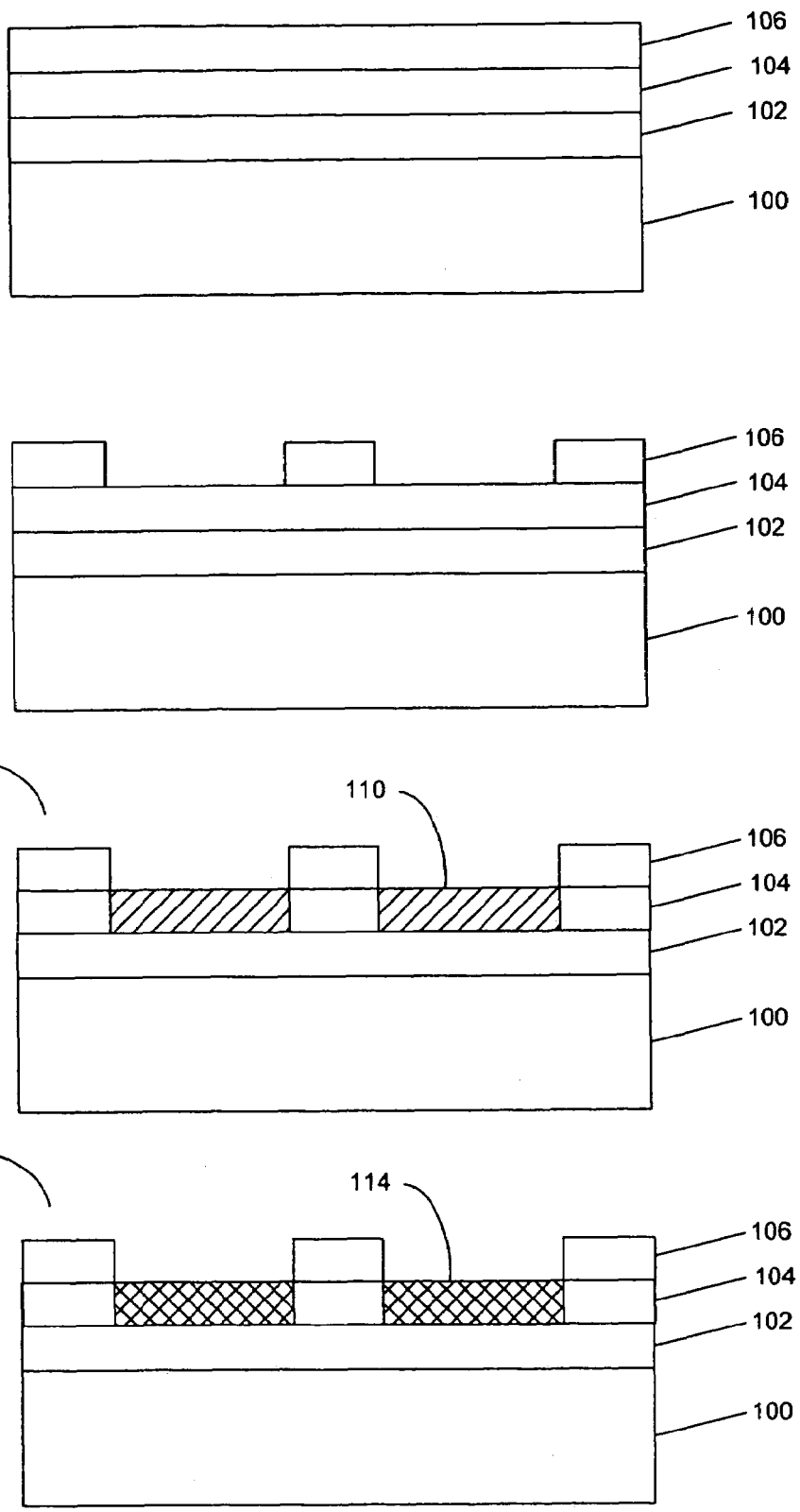
FIG. 8 is a schematic illustration of a process flow for forming a patterned Au-NST nanocomposite.
Figures 9A, 9B, 9C, 9D, 9E, 9F:
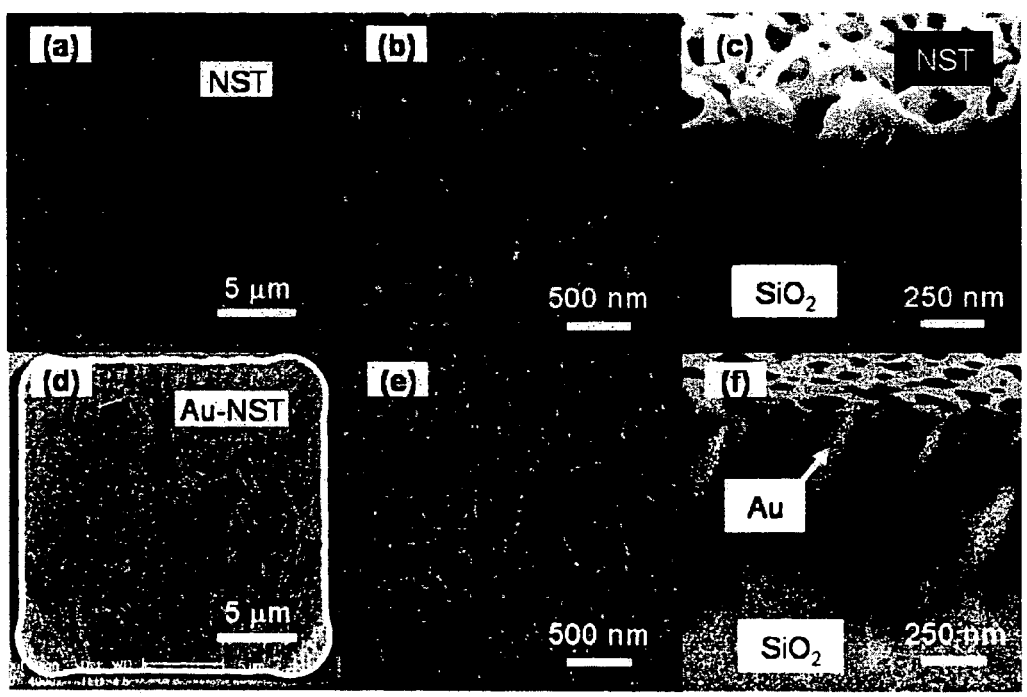
FIGS. 9(a)-9(f) are SEM images of the morphology of NST and Au-NST patterns.

FIG. 8 shows a schematic of the process flow for fabricating the interpenetrating Au-NST network nanocomposites.

First, layer 102 is deposited on substrate 100, Ti layer 104 is deposited on layer 102, and mask layer 106 is deposited on layer 104. Mask layer 106 is patterned using photoresist as described with respect to FIG. 1, and porous NST patterns 110 are formed by oxidizing Ti layer 104 as described above.

The pores of NST patterns 110 are then infiltrated with Au to form nanocomposite layer 114 using electroless deposition. Although Au and electroless deposition is used in the above embodiment, other suitable materials and methods may be used without departing from the scope of the present invention.

FIGS. 9(a)-9(f) show the morphology of the NST pads before (a-c) and after (d-f) Au infiltration in accordance with the present invention.

Figure 10:
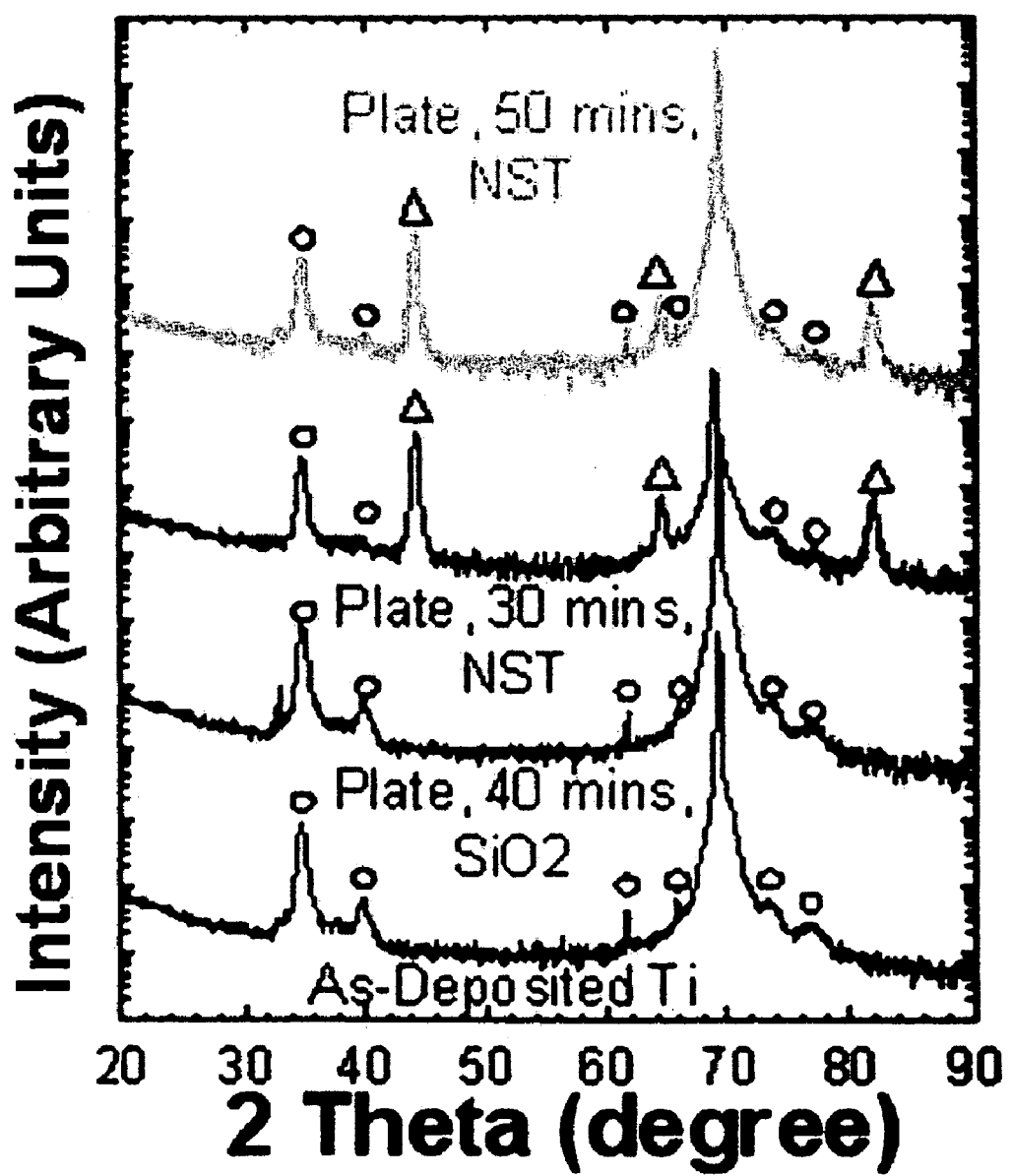
FIG. 10 graphically illustrates Au reflections on NST.

The highly selective deposition of Au on NST pads, no Au deposition occurs on the $SiO_2$ mask, is evident in FIG. 10 that shows XRD spectra taken at NST 110 and $SiO_2$ mask regions 106 after Au plating. XRD studies of patterned NST pad arrays indicate that Au was deposited on NST pads 110 only and not on the $SiO_2$ mask 106. Such selective deposition was observed on amorphous and crystalline NST 110, corresponding to the as-aged and annealed conditions, respectively.

FIG. 10 shows the XRD spectra of amorphous NST after plating.

The XRD spectra of FIG. 10 demonstrates the selective deposition of Au after various immersion times in the electroless plating bath. A comparison of XRD spectra of the sample 112 after Au plating indicates the presence of three peaks at 2θ values of 44.18, 64.46 and 81.76 degrees on the NST pad 306 array. These peaks, however, are not present in spectra collected from the $SiO_2$ mask 106 region. These observations strongly indicate that Au has deposited only in the pores of the NST pads 306 and not on the surface of $SiO_2$ mask 106. The three peaks observed can be assigned to the {200}, {220} and {222} of Au. Ti films 104 on the patterned and blanket samples used for XRD studies were deposited in different evaporation machines that resulted in different textures as reflected in the as-deposited XRD spectra. Prior studies indicate that Ti surface texture has little effect on the morphology of NST 110 formed.

FIGS. 11(a)-11(d) illustrate the results of XPS studies.

All spectra were referenced to C1s peak at 285.0 eV. FIG. 11(a) is a high resolution scan of the Ti2p peaks of unpatterned NST film formed on PECVD $SiO_2$ on Si substrate after annealing at 8 hr for 300° C. Similar results were obtained from NST formed on a PECVD $SiO_2$ coated glass substrate. Assuming a Tougaard, background, fitting to the raw spectra was done using Gaussian-Lorentzian components using a commercial XPS analysis software (CasaXPS). From the analysis, binding energies of $Ti2p_{3/2}$ and $Ti2p_{1/2}$ were found to be 458.9 and 464.8 eV, respectively. These values are close to those reported in the literature for $TiO_2$ of 458.9 and 464.6 eV for $Ti2p_{3/2}$ and $Ti2p_{1/2}$, respectively, and confirm the formation of $TiO_2$ after annealing.

FIG. 11(b) shows XPS spectra for binding energies from 55 to 110 eV of unpatterned NST film before and after 5 minutes of Au plating. Before plating only Si2p signal with a peak at 101.3 eV was detected. However, three additional peaks were detected after plating. Assignment of these peaks was similarly done using CasaXPS. Two peaks at binding energies of 84.60 and 88.16 eV are assigned to Au $4f_{7/2}$ and Au $4f_{5/2}$.

These experimental values of Au $4f_{7/2}$ and Au $4f_{3/2}$ obtained are consistently higher, by 0.38 and 0.22 eV respectively, but close to corresponding values reported in the literature; which range from 83.70 to 84.25 ev for Au $4f_{7/2}$ and 87.71 to 87.94 ev for Au $4f_{5/2}$ of elemental Au. As such, electrodeposited Au is in the elemental form, in agreement with XRD results.

The peak at 63.13 eV in FIG. 11(b) is assigned to Na 2s; another peak, which is assigned to Na 1s, at 1071.58 eV was also observed after plating. Entrapment of sodium in a metal layer deposited from a plating bath has been shown that similarly used $Na_2EDTA$ as a chelating agent. Na 1s binding energies of adsorbed sodium atoms, in the presence of coadsorbed iodine atoms, on Au(100) surfaces, has been shown in the art.

In the absence of iodine and when coverage of Na atoms on the Au surface is 0.09 of a monolayer, the Na 1s binding energy was determined to be about 1071.05 eV, which is close to that obtained in the present study. The formation of Au—Na phases after plating can be discounted since additional XRD reflections detected after plating can be assigned only to elemental Au. It may be concluded that Au has been deposited in pores of NST pads and Na, at a dilute concentration, incorporated into the Au layer during plating.

Results of area-mode XPS studies confirm that Au deposits selectively on NST. FIGS. 11(c) and 11(d) show, respectively, Si 2p and Au 4f signals of one region of an NST pad array after electroless Au plating. The results of the area-mode XPS are presented in gray-scale in which areas with higher concentration of a chemical species appear brighter. In addition, it is noted that XPS is a technique sensitive to chemical species on the first few nanometers from the surface only. From FIG. 11(c), the strong Si2p signal implies that very little, if any, Au has deposited on the $SiO_2$ mask surface. This is confirmed in FIG. 11(d) that shows Au 4f signal only in areas that correspond to those of NST pads 306. These XPS results are in agreement with those of XRD studies and demonstrate that Au has been deposited selectively on NST 110 only.

Process Chart

Figure 12:
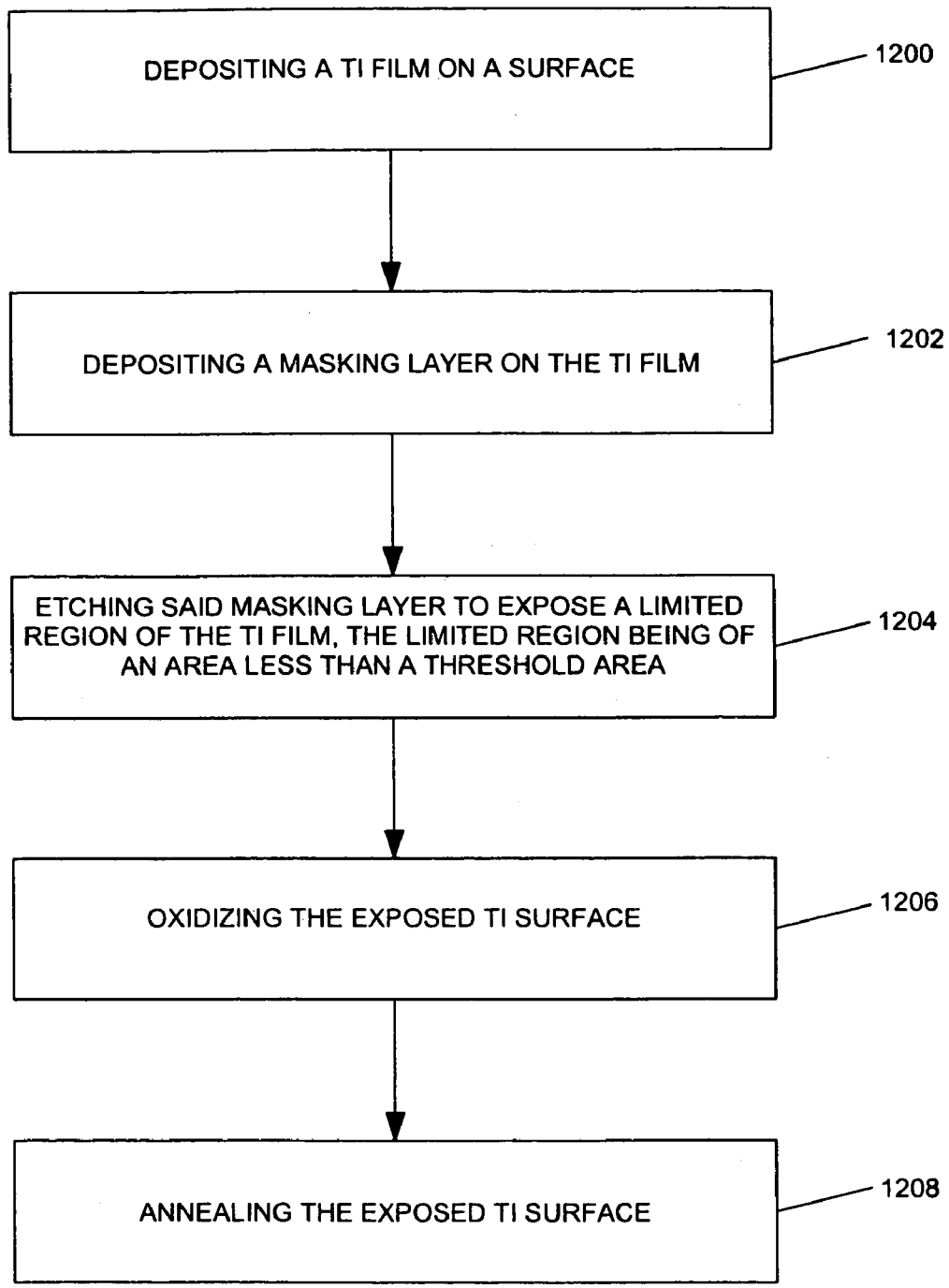
FIG. 12 illustrates process steps used in making a device in accordance with the present invention.

FIG. 12 illustrates process steps used in making a device in accordance with the present invention.

Box 1200 illustrates depositing a Ti film on a surface.

Box 1202 illustrates depositing a masking layer on the Ti film.

Box 1204 illustrates etching the masking layer to expose a limited region of the Ti film, the limited region being of an area less than a threshold area.

Box 1206 illustrates oxidizing the exposed limited region of the Ti film.

Box 1208 illustrates annealing the exposed limited region of the Ti film.

Related References

The following references are also herein incorporated by reference: "Formation of Nanostructured Titania: Effect of Thickness on Oxidation Kinetics of Titanium Thin Films in Aqueous Hydrogen Peroxide," D. M DeRosa, Abu Samah Zuruzi, and Noel C. MacDonald, Advanced Engineering Materials 2006, 8, No. 1-2, Pgs. 77-80; "Highly sensitive gas sensor based on integrated Mania nanosponge arrays," A. S. Zuruzi et al., Applied Physics Letters 88, 102904, 2006; "Nanostructured TiO2 thin films as porous cellular interfaces," Abu Samah Zuruzi et al., Nanotechnology 17 (2006) pages 531-535; and "Fabrication and characterization of patterned micrometre scale interpenetrating Au—TiO2 network nanocomposites," Abu Samah Zuruzi et al., Nanotechnology 16 (2005) pages 1029-1034.

Conclusion

In summary, the present invention describes a device and method for forming nanostructured Mania. A method in accordance with the present invention comprises depositing a Ti film on a surface, depositing a masking layer on the Ti film, etching said masking layer to expose a limited region of the Ti film, the limited region being of an area less than a threshold area, oxidizing the exposed limited region of the Ti film, and annealing the exposed limited region of the Ti film. Such a method further optionally includes oxidizing the exposed limited region of the Ti film includes aging the exposed limited region of the Ti film using an aqueous hydrogen peroxide solution, the threshold area has a dimension of about 20 µm, adding dopants to the Ti film, adding dopants includes soaking the exposed limited region of the Ti film in a dopant-containing solution after aging, adding dopants includes coating the exposed limited region of the Ti film with dopant species after annealing, depositing and patterning a metal electrode on the exposed limited region of the Ti film after annealing, infiltrating the exposed limited region of the Ti film with an electrically conductive metal to form an interpenetrating network nanocomposite, etching the masking layer exposes a plurality of limited regions of the Ti film to form an array of pads, selectively metallizing the array of pads to interconnect the pads, infiltrating a metal into pores in the exposed limited region of the Ti film, depositing the Ti film on a surface comprises depositing the Ti film on a flexible substrate, and etching the masking layer exposes a plurality of limited regions of the Ti film to form an array of pads, the method further including metallizing the array to interconnect the pads.

A patterned, crack-free nanostructural titania (NST) element in accordance with the present invention comprises a substrate, a Ti film deposited on the substrate, and a masking layer having at least one aperture exposing a region of the Ti film, the region having a dimension of about 20 µm; wherein the exposed region of the Ti film is oxidized to create at least one porous $TiO_2$ region. Such a device further optionally includes an electrical contact on the porous $TiO_2$ region, the substrate being flexible, an electrically conducting metal infiltrated in the porous $TiO_2$ region, the exposed region of the Ti film being oxidized to create a plurality of porous $TiO_2$ for forming an array of pads, the porous $TiO_2$ region further comprises pores ranging in diameter from about 15 nm to about 150 nm, and adding dopants to the Ti film.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but by the claims appended hereto and the equivalents thereof.

What is claimed is:

1. A method of fabricating patterned, crack free nanostructured Titania (NST) comprising:
    depositing a Ti film on a surface;
    depositing a masking layer on the Ti film;
    etching said masking layer to expose a limited region of the Ti film, the limited region being of an area less than a threshold area in order to reduce cracking of the Ti film, wherein the threshold area has a dimension of at least 20 µm;
    oxidizing the exposed limited region of the Ti film; and
    annealing the exposed limited region of the Ti film.

2. The method of claim 1, wherein oxidizing the exposed limited region of the Ti film includes aging the exposed limited region of the Ti film using an aqueous hydrogen peroxide solution.

3. The method of claim 2, wherein the threshold area has a dimension of about 20 μm.

4. The method of claim 2, further including adding dopants to the Ti film.

5. The method of claim 4, wherein adding the dopants includes soaking the exposed limited region of the Ti film in a dopant-containing solution after aging.

6. The method of claim 4, wherein adding the dopants includes coating the exposed limited region of the Ti film with dopant species after the annealing.

7. The method of claim 1, further including depositing and patterning a metal electrode on the exposed limited region of the Ti film after the annealing.

8. The method of claim 1, further including infiltrating the exposed limited region of the Ti film with an electrically conductive metal to form an interpenetrating network nanocomposite.

9. The method of claim 1, wherein etching the masking layer exposes a plurality of limited regions of the Ti film to form an array of pads.

10. The method of claim 9, further including selectively metallizing the array of pads to interconnect the pads.

11. The method of claim 1, further including infiltrating a metal into pores in the exposed limited region of the Ti film.

12. The method of claim 1, wherein depositing the Ti film on the surface comprises depositing the Ti film on a flexible substrate.

13. The method of claim 1, wherein etching the masking layer exposes a plurality of limited regions of the Ti film to form an array of pads, the method further including metallizing the array to interconnect the pads.

14. A patterned, crack-free nanostructural titania (NST) element comprising:
   a substrate;
   a Ti film deposited on the substrate; and
   a masking layer having at least one aperture exposing a region of the Ti film, the region having a dimension of about 20 μm, wherein the exposed region of the Ti film is oxidized to create at least one porous $TiO_2$ region.

15. The NST element of claim 14, further including an electrical contact on the porous $TiO_2$ region.

16. The NST element of claim 15, wherein the substrate is flexible.

17. The NST element of claim 15, further comprising an electrically conducting metal infiltrated in the porous $TiO_2$ region.

18. The NST element of claim 15, wherein the exposed region of the Ti film is oxidized to create a plurality of porous $TiO_2$ regions for forming an array of pads.

19. The NST element of claim 15, wherein the porous $TiO_2$ region further comprises pores ranging in diameter from about 15 nm to about 150 nm.

20. The NST element of claim 15, further comprising adding dopants to the Ti film.

* * * * *

UNITED STATES PATENT AND TRADEMARK OFFICE
CERTIFICATE OF CORRECTION

PATENT NO. : 7,718,552 B2  Page 1 of 1
APPLICATION NO. : 11/397165
DATED : May 18, 2010
INVENTOR(S) : Zuruzi Abu Samah et al.

It is certified that error appears in the above-identified patent and that said Letters Patent is hereby corrected as shown below:

Column 1

Line 13, please insert the following:

--STATEMENT REGARDING FEDERALLY SPONSORED RESEARCH OR DEVELOPMENT

The present invention was made with Government support under Grant No. W9113M-04-1-001, awarded by the Department of Defense. The Government has certain rights in this invention.--

Signed and Sealed this

Twentieth Day of July, 2010

David J. Kappos
*Director of the United States Patent and Trademark Office*